(12) United States Patent
Mastroianni

(10) Patent No.: US 8,697,902 B2
(45) Date of Patent: *Apr. 15, 2014

(54) PREPARATION OF NITRILES FROM ETHYLENICALLY UNSATURATED COMPOUNDS

(75) Inventor: Sergio Mastroianni, Lyons (FR)

(73) Assignee: Rhodia Operations, Aubervilliers (FR)

( * ) Notice: Subject to any disclaimer, the term of this patent is extended or adjusted under 35 U.S.C. 154(b) by 266 days.

This patent is subject to a terminal disclaimer.

(21) Appl. No.: 12/999,350

(22) PCT Filed: Jun. 5, 2009

(86) PCT No.: PCT/EP2009/056917
§ 371 (c)(1),
(2), (4) Date: Jan. 27, 2011

(87) PCT Pub. No.: WO2009/153172
PCT Pub. Date: Dec. 23, 2009

(65) Prior Publication Data
US 2011/0118499 A1    May 19, 2011

(30) Foreign Application Priority Data
Jun. 17, 2008 (FR) ..................... 08 03373

(51) Int. Cl.
C07C 253/00 (2006.01)
C07F 9/02 (2006.01)

(52) U.S. Cl.
USPC ........................... 558/332; 549/516; 548/412

(58) Field of Classification Search
USPC .............................. 549/5, 6; 558/332; 548/412
See application file for complete search history.

(56) References Cited

U.S. PATENT DOCUMENTS

| 6,153,758 A | 11/2000 | Sannicolo et al. |
| 7,105,696 B2 * | 9/2006 | Burattin et al. ............... 558/338 |
| 2004/0116713 A1 | 6/2004 | Beller et al. |
| 2009/0227801 A1 * | 9/2009 | Ahlers et al. ................. 548/101 |

FOREIGN PATENT DOCUMENTS

| FR | 2830530 A1 | 4/2003 |
| WO | WO 02/053527 A1 | 7/2002 |

OTHER PUBLICATIONS

International Search Report corresponding to PCT/EP 2009/056917.

* cited by examiner

*Primary Examiner* — Nyeemah A Grazier
(74) *Attorney, Agent, or Firm* — Dentons US LLP

(57) ABSTRACT

A process for the hydrocyanation of a hydrocarbon-based compound having at least one site of ethylenic unsaturation into a nitrile compound includes reaction thereof, in a liquid medium, with hydrogen cyanide in the presence of a catalyst containing a metal element selected from among the transition metals and an organophosphorus ligand, wherein the organophosphorus ligand is a compound of formula (I):

$$\left[ (R_1)_m - \underset{3-n}{\bigcirc} \right] - P - Z_n \qquad (I)$$

The subject process is particularly useful for the synthesis of adiponitrile from butadiene.

12 Claims, No Drawings

PREPARATION OF NITRILES FROM ETHYLENICALLY UNSATURATED COMPOUNDS

CROSS-REFERENCE TO PRIOR APPLICATIONS

This application is the U.S. National Stage of PCT/EP 2009/056917, filed Jun. 5, 2009 and designating the United States (published in the French language on Dec. 23, 2009, as WO 2009/153172 A1; the title and abstract were also published in English), which claims priority under 35 U.S.C. §119 of FR 0803373, filed Jun. 17, 2008, each hereby expressly incorporated by reference in its entirety and each assigned to the assignee hereof.

The present invention relates to a process for the hydrocyanation of ethylenically unsaturated organic compounds to give compounds comprising at least one nitrile function.

It relates more particularly to the hydrocyanation of diolefins such as butadiene or of substituted olefins such as alkenenitriles, for instance pentenenitriles.

French Patent No. 1 599 761 describes a process for preparing nitriles by the addition of hydrocyanic acid to organic compounds having at least one ethylenic double bond, in the presence of a catalyst comprising nickel and an organophosphorrus ligand, a triaryl phosphite. This reaction can be carried out in the presence or absence of a solvent.

When a solvent is used, it is preferably a hydrocarbon, such as benzene or xylenes, or a nitrile such as acetonitrile.

The catalyst used is an organic nickel complex, containing ligands such as phosphines, arsines, stibines, phosphites, arsenites or antimonites.

The presence of a promoter for activating the catalyst, such as a boron compound or a metal salt, generally a Lewis acid, is also recommended in said patent.

Many other catalytic systems have been proposed, generally comprising organophosphorus compounds belonging to the phosphite, phosphonite, phosphinite and phosphine family. These organophosphorus compounds may comprise one atom of phosphorus per molecule, and are described as monodentate ligands. They may comprise several phosphorus atoms per molecule, and they are then known as polydentate ligands; more particularly, many ligands containing two phosphorus atoms per molecule (bidentate ligands) have been described in many patents.

However, the search for new catalytic systems which give greater performance levels, both in terms of catalytic activity and in terms of stability, is still ongoing.

One of the objectives of the present invention is to propose a new family of ligands which makes it possible to obtain, with the transition metals, catalytic systems which exhibit good catalytic activity in the hydrocyanation reaction.

To this effect, the present invention proposes a process for the hydrocyanation of a hydrocarbon-based compound comprising at least one ethylenic unsaturation, by reaction, in a liquid medium, with hydrogen cyanide in the presence of a catalyst comprising a metal element chosen from transition metals and one or more organophosphorus ligands, characterized in that the organophosphorus ligand comprises at least one compound corresponding to general formula (I):

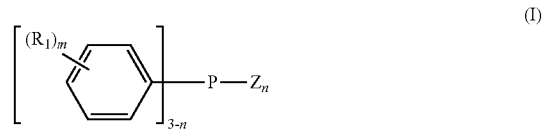

in which:
Z represents an aromatic or nonaromatic, substituted or unsubstituted, 5- or 6-atom cyclic group containing a nitrogen or sulphur atom and such that the bond with the phosphorus is borne by the carbon in the alpha-position with respect to the heteroatom,
n represents an integer from 1 to 3,
m represents an integer from 0 to 5,
the $R_1$ radical represents a hydrogen atom, a linear or branched alkyl radical, that may contain heteroatoms, having from 1 to twelve carbon atoms, a substituted or unsubstituted aromatic or cycloaliphatic radical that may comprise heteroatoms, a carbonyl, alkoxycarbonyl or alkoxy radical, a halogen atom, a nitrile group or a haloalkyl group having from one to twelve carbon atoms.

Z is preferably a thienyl, pyrryl or pyridyl group, and more preferably a thienyl group.

Advantageously, the organophosphorus ligand is a compound corresponding to general formula (I) or a mixture of monodentate organophosphine compounds, at least one compound of which corresponds to general formula (I).

According to the invention, the composition of the catalytic system may be represented by general formula (II) (this formula does not correspond to the structure of the compounds and complexes present in the catalytic system):

in which:
M is a transition metal,
$L_f$ represents at least one organophosphorus ligand of formula (I),
t represents a number between 1 and 10 (limits included).

The metals M which may be complexed are, in general, all the transition metals of groups 1b, 2b, 3b, 4b, 5b, 6b, 7b and 8 of the Periodic Table of Elements, as published in "Handbook of Chemistry and Physics, 51st Edition (1970-1971)" of The Chemical Rubber Company.

Among these metals, mention may more particularly be made of the metals that can be used as catalysts in hydrocyanation reactions. Thus, by way of nonlimiting examples, mention may be made of nickel, cobalt, iron, ruthenium, rhodium, palladium, osmium, iridium, platinum, copper, silver, gold, zinc, cadmium and mercury. Nickel is the preferred element for the hydrocyanation of unsaturated nitriles and olefins.

As suitable compounds of general formula (I), mention may be made, by way of nonlimiting examples, of (2-thienyl)diphenylphosphine, di(2-thienyl)phenylphosphine, tri(2-thienyl)phosphine, (2-pyrryl)diphenylphosphine, di(2-pyrryl)phenylphosphine, tri(2-pyrryl)phosphine, (2-pyridyl)diphenylphosphine, di(2-pyridyl)phenylphosphine and tri(2-pyridyl)phosphine.

For the preparation of the thienylphosphines and pyrrylphosphines according to general formula (I), reference may be made, for example, to the article by V. K. Issleib and A. Brack published in Zeitschrift für anorganische und allgemeine Chemie, 1957, 292, pages 245 to 253. For the synthesis of the pyridylphosphines according to general formula (I), reference may be made, for example, to Patent EP0499328.

The preparation of the catalytic systems comprising compounds of general formula (I), optionally as a mixture with other monodentate organophosphines, can be carried out by bringing a solution of a compound of the chosen metal, for example, nickel, into contact with a solution of the organophosphorus compound of the invention.

The compound of the metal can be dissolved in a solvent. The metal can occur, in the compound used, either in the oxidation state that it will have in the organometallic complex, or in a higher oxidation state.

By way of example, it may be indicated that, in the organometallic complexes of the invention, rhodium is in the oxidation state (I), ruthenium in the oxidation state (II), platinum in the oxidation state (0), palladium in the oxidation state (0), osmium in the oxidation state (II), iridium in the oxidation state (I) and nickel in the oxidation state (0).

If, during the preparation of the organometallic complex, the metal is used in a higher oxidation state, it can be reduced in situ.

Among the complexes of metals M that can be used for the preparation of the organometallic complexes, mention may be made, by way of nonlimiting examples, of the following nickel compounds:

compounds in which the nickel is in the zero oxidation state, such as potassium tetracyanonickelate $K_4[Ni(CN)_4]$, bis(acrylonitrile)nickel(0), bis(1,5-cyclooctadiene) nickel (also known as $Ni(cod)_2$) and derivatives comprising ligands, such as tetrakis(triphenylphosphine) nickel(0);

nickel compounds, such as carboxylates (in particular the acetate), carbonate, bicarbonate, borate, bromide, chloride, citrate, thiocyanate, cyanide, formate, hydroxide, hydrophosphite, phosphite, phosphate and derivatives, iodide, nitrate, sulphate, sulphite, arylsulphonates and alkylsulphonates.

When the nickel compound used corresponds to an oxidation state of the nickel of greater than 0, a reducing agent for nickel which reacts preferentially with the latter under the reaction conditions is added to the reaction medium. This reducing agent may be organic or inorganic. As nonlimiting examples, mention may be made of borohydrides, such as $NaBH_4$ or $KBH_4$, Zn powder, magnesium or hydrogen.

When the nickel compound used corresponds to the 0 oxidation state of nickel, it is also possible to add a reducing agent of the type of those mentioned above, but this addition is not essential.

When an iron compound is used, the same reducing agents are suitable. In the case of palladium, the reducing agents may in addition be components of the reaction medium (phosphine, solvent, olefin).

The organic compounds comprising at least one ethylenic double bond more particularly used in the present process are diolefins, such as butadiene, isoprene, 1,5-hexadiene or 1,5-cyclooctadiene, ethylenically unsaturated aliphatic nitriles, particularly linear pentenenitriles, such as 3-pentenenitrile or 4-pentenenitrile, monoolefins, such as styrene, methylstyrene, vinylnaphthalene, cyclohexene or methylcyclohexene, and mixtures of several of these compounds.

The pentenenitriles may contain, in addition to the 3-pentenenitrile and the 4-pentenenitrile, amounts, generally minor amounts, of other compounds, such as 2-methyl-3-butenenitrile, 2-methyl-2-butenenitrile, 2-pentenenitrile, valeronitrile, adiponitrile, 2-methylglutaronitrile, 2-ethylsuccinonitrile or butadiene, for example originating from the earlier hydrocyanation reaction of butadiene to give unsaturated nitriles.

Specifically, during the hydrocyanation of butadiene, not insignificant amounts of 2-methyl-3-butenenitrile and of 2-methyl-2-butenenitrile are formed with the linear pentenenitriles.

The catalytic system used for the hydrocyanation according to the process of the invention can be prepared before it is introduced into the reaction medium, for example by addition to the phosphine of formula (I), alone or dissolved in a solvent, of the appropriate amount of compound of the chosen transition metal and, optionally, of the reducing agent. It is also possible to prepare the catalytic system "in situ" by simple addition of the phosphine and of the compound of the transition metal to the hydrocyanation reaction medium, before or after the addition of the compound to be hydrocyanated.

The amount of nickel compound or of compound of another transition metal used is chosen in order to obtain a concentration, as moles of transition metal per mole of organic compounds to be hydrocyanated or isomerized, of between $10^{-4}$ and 1, and preferably between 0.005 and 0.5 mol of nickel or of the other transition metal used.

The amount of organophosphine compounds including the organophosphines of formula (I) used to form the catalyst is chosen such that the number of moles of this compound relative to 1 mol of transition metal is from 0.5 to 100 and preferably from 2 to 50.

Although the reaction is generally carried out without solvent, it may be advantageous to add an inert organic solvent. The solvent can be a solvent for the catalyst which is miscible with the phase comprising the compound to be hydrocyanated at the hydrocyanation temperature. By way of examples of such solvents, mention may be made of aromatic, aliphatic or cycloaliphatic hydrocarbons.

The hydrocyanation reaction is generally carried out at a temperature of 10° C. to 200° C., and preferably of 30° C. to 120° C. It can be carried out in a single-phase medium.

The process of the invention can be carried out continuously or batchwise.

The hydrogen cyanide used can be prepared from metal cyanides, in particular sodium cyanide, or cyanohydrins, such as acetone cyanohydrin, or by any other known synthetic process, such as the Andrussov process which consists in reacting methane with ammonia and air.

The hydrogen cyanide, free of water, is introduced into the reactor in the gaseous form or in the liquid form. It can also be dissolved beforehand in an organic solvent.

In the context of a batchwise implementation, it is possible in practice to charge, to a reactor purged beforehand using an inert gas (such as nitrogen or argon), either a solution containing all or a portion of the various constituents, such as the phosphine of formula I, the transition metal (nickel) compound, the optional reducing agent and the optional solvent, or said constituents separately. Generally, the reactor is then brought to the chosen temperature, and the compound to be hydrocyanated is then introduced. The hydrogen cyanide is then itself introduced, preferably continuously and uniformly.

When the reaction (the progress of which can be monitored by assaying withdrawn samples) is complete, the reaction mixture is withdrawn after cooling and the reaction products are isolated and separated, for example by distillation.

Advantageously, the synthesis of dinitriles, such as adiponitrile, from diolefins (butadiene) is obtained in two successive stages. The first stage consists in hydrocyanating a double bond of the diolefin so as to obtain an unsaturated mononitrile. The second stage consists in hydrocyanating the unsaturation of the mononitrile so as to obtain the corresponding dinitrile(s). These two stages are generally carried out with a catalytic system comprising an organometallic complex of the same nature. However, the organophosphorus compound/metal element ratios and concentration of the catalyst may be different. In addition, it is preferable to combine a cocatalyst or promoter with the catalytic system in the second stage. This cocatalyst or promoter is generally a Lewis acid.

The Lewis acid used as cocatalyst makes it possible, in particular, in the case of hydrocyanation of ethylenically unsaturated aliphatic nitriles, to improve the linearity of the dinitriles obtained, i.e. the percentage of linear dinitrile relative to all the dinitriles formed, and/or to increase the activity and the lifetime of the catalyst, The term "Lewis acid" is intended to mean, in the present text, according to the usual definition, compounds which accept electron pairs.

Use may in particular be made of the Lewis acids mentioned in the book edited by G. A. Olah, "Friedel-Crafts and related Reactions", volume I, pages 191 to 197 (1963).

The Lewis acids which can be used as cocatalysts in the present process are chosen to from the compounds of elements from groups Ib, IIb, IIIa, IIIb, IVa, IVb, Va, Vb, VIb, VIIb and VIII of the Periodic Table of Elements. These compounds are most commonly salts, in particular halides, such as chlorides or bromides, sulphates, sulphonates, halosulphonates, perhaloalkylsulphonates, in particular fluoroalkylsulphonates or perfluoroalkylsulphonates, carboxylates and phosphates.

By way of nonlimiting examples of such Lewis acids, mention may be made of zinc chloride, zinc bromide, zinc iodide, manganese chloride, manganese bromide, cadmium chloride, cadmium bromide, stannous chloride, stannous bromide, stannous sulphate, stannous tartrate, indium trifluoromethylsulphonate, chlorides or bromides of rare earth elements, such as lanthanum, cerium, praseodymium, neodymium, samarium, europium, gadolinium, terbium, dysprosium, hafnium, erbium, thallium, ytterbium and lutetium, cobalt chloride, ferrous chloride or yttrium chloride.

Use may also be made, as Lewis acid, of organometallic compounds such as triphenylborane or titanium isopropoxide or the compounds described in the unpublished French Patent Application filed on 25 Jan. 2008 under No, 08 00381.

It is, of course, possible to use mixtures of several Lewis acids.

Among Lewis acids, preference is most particularly given to zinc chloride, zinc bromide, stannous chloride, stannous bromide, triphenylborane, and zinc chloride/stannous chloride mixtures.

The Lewis acid cocatalyst used generally represents from 0.01 to 50 mol per mole of transition metal compound, more particularly of nickel compound, and preferably from 1 to 10 mol per mole.

The unsaturated mononitriles used in this second stage are advantageously linear pentenenitriles, such as 3-pentenenitrile or 4-pentenenitrile, and mixtures thereof.

These pentenenitriles may contain amounts, generally minor amounts, of other compounds, such as 2-methyl-3-butenenitrile, 2-methyl-2-butenenitrile or 2-pentenenitrile.

The catalytic solution used for the hydrocyanation in the presence of a Lewis acid can be prepared before it is introduced into the reaction medium, for example by addition, to the phosphine of formula (I), of the appropriate amount of compound of the transition metal chosen, of the Lewis acid and, optionally, of the reducing agent. It is also possible to prepare the catalytic solution "in situ" by simple addition of these various constituents to the reaction medium.

It is also possible, under the conditions of the hydrocyanation process of the present invention, and in particular by performing the procedure in the presence of the catalyst described above comprising at least one compound of formula (I) and at least one compound of a transition metal, to carry out, in the absence of hydrogen cyanide, the isomerization of 2-methyl-3-butenenitrile to give pentenenitriles, and more generally of branched unsaturated nitriles to give linear unsaturated nitriles.

The 2-methyl-3-butenenitrile subjected to the isomerization according to the invention can be used alone or as a mixture with other compounds. Thus, 2-methyl-3-butenenitrile can be introduced as a mixture with 2-methyl-2-butenenitrile, 4-pentenenitrile, 3-pentenenitrile, 2-pentenenitrile or butadiene.

It is particularly advantageous to treat the reaction mixture originating from the hydrocyanation of butadiene with HCN in the presence of at least one compound of formula (I) and of at least one compound of a transition metal, more preferably of a nickel compound in which the nickel is in the zero oxidation state, as defined above. In the context of this preferred variant, since the catalytic system is already present for the butadiene hydrocyanation reaction, it is sufficient to halt any introduction of hydrogen cyanide in order to allow the isomerization reaction to take place. It is possible, if appropriate, in this variant, to carry out a gentle flushing of the reactor using an inert gas, such as nitrogen or argon, for example, in order to drive off the hydrocyanic acid which might still be present.

The isomerization reaction is generally carried out at a temperature between 10° C. and 200° C., and preferably between 60° C. and 140° C.

In the preferred case of an isomerization immediately following the butadiene hydrocyanation reaction, it will be advantageous to carry out the reaction at a temperature at which the hydrocyanation was carried out, or slightly higher.

As for the process for the hydrocyanation of ethylenically unsaturated compounds, the catalytic system used for the isomerization can be prepared before it is introduced into the reaction medium, for example by mixing the compound of formula (I), the appropriate amount of compound of the chosen transition metal and, optionally, of the reducing agent. It is also possible to prepare the catalytic system "in situ" by simple addition of these various constituents to the reaction medium. The amount of transition metal compound, and more particularly nickel compound, used, and also the amount of compound of formula (I), are the same as for the hydrocyanation reaction.

Although the isomerization reaction is generally carried out without solvent, it can be advantageous to add an inert organic solvent that can be subsequently used as extraction solvent. This is in particular the case when such a solvent was used in the reaction for hydrocyanation of butadiene used to prepare the medium subjected to the isomerization reaction. Such solvents can be chosen from those that were mentioned above for the hydrocyanation.

However, the preparation of dinitrile compounds by hydrocyanation of an olefin such as butadiene can be carried out using a catalytic system in accordance with the invention for the stages of formation of the unsaturated nitriles and the stage of isomerization above, it being possible for the reaction for the hydrocyanation of the unsaturated nitriles to give dinitriles to be carried out with a catalytic system in accordance with the invention or any other catalytic system already known for this reaction.

Likewise, the reaction for the hydrocyanation of the olefin to give unsaturated nitriles and the isomerization of the latter can be carried out with a catalytic system different from that of the invention, the stage of hydrocyanation of the unsaturated nitriles to give dinitriles being carried out with a catalytic system in accordance with the invention.

Other details and advantages of the invention will be illustrated by the examples given below, only by way of indication and which are not limiting in nature.

Abbreviations used
cod: cyclooctadiene
$Ni(cod)_2$: bis(1,5-cyclooctadiene)nickel
3PN: 3-pentenenitrile
AdN: adiponitrile
ESN: ethylsuccinonitrile
MGN: methylglutaronitrile
DN: dinitrile compounds (AdN, MGN or ESN)
TIBAO: tetraisobutyldialuminoxane
Mes: mesityl group (2,4,6-trimethylphenyl)
Ph: phenyl group
RY(DN): real yield of dinitriles corresponding to the ratio of the number of moles of dinitriles formed to the number of moles of 3PN introduced
Linearity (L): ratio of the number of moles of AdN formed to the number of moles of dinitriles formed (sum of the moles of AdN, ESN and MGN).

The following compounds: 3PN, $Ni(cod)_2$, $ZnCl_2$, TIBAO, diphenylboron anhydride ($Ph_2BOPh_2$), tris(2-thienyl)phosphine, tris(2-furyl)phosphine and (2-pyridyl)diphenylphosphine are known products that are commercially available.

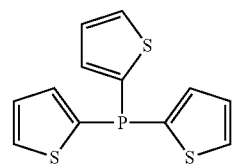 [SMILES: c1csc(P(c2cccs2)c2cccs2)c1]

(2-pyridyl)diphenylphosphine: sold by the company Aldrich

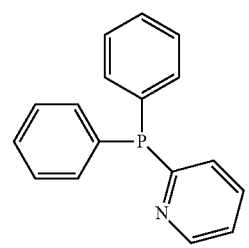 [SMILES: c1ccc(P(c2ccccc2)c2ccccn2)cc1]

The mixture is brought to 70° C. with stirring. Acetone cyanohydrin is fed into the reaction medium via a syringe driver at a flow rate of 0.45 ml per hour. After 3 hours, the injection is stopped. The mixture is cooled to ambient temperature, diluted with acetone, and analysed by gas chromatography.

The results are collated in the table below:

TABLE 1

| Examples 0 to 7 | | | | | |
|---|---|---|---|---|---|
| Example | Ligand A | Lewis acid | Lewis acid/Ni | Linearity | RY (DN) |
| 0 (comparative) | Tris(2-furyl)phosphine | TiBAO | 0.5 | 52.7 | 30.4 |
| 1 | Tris(2-thienyl)phosphine | $ZnCl_2$ | 1 | 62.5 | 75.8 |
| 2 | Tris(2-thienyl)phosphine | TiBAO | 0.5 | 64.1 | 70.6 |
| 3 | Tris(2-thienyl)phosphine | $Ph_2BOBPh_2$ | 0.5 | 84.7 | 32.3 |
| 4 | Tris(2-thienyl)phosphine | $Mes_2BOZnEt$* | 0.5 | 65 | 9.2 |
| 5 | (2-pyridyl)diphenylphosphine | $ZnCl_2$ | 1 | 63.6 | 9.5 |
| 6 | (2-pyridyl)diphenylphosphine | TiBAO | 0.5 | 62.8 | 16.5 |
| 7 | (2-pyridyl)diphenylphosphine | $Ph_2BOBPh_2$ | 0.5 | 74.4 | 8.1 |

*The synthesis of this Lewis acid is described in the unpublished French patent application filed on 25 Jan. 2008 under number 08 00381.

EXAMPLES 0 TO 7

Hydrocyanation of 3-PN to Give AdN

The tests are carried out according to the following procedure:

The following are successively charged, under an argon atmosphere, to a 60 ml glass tube of Shott type, equipped with a septum stopper:
  ligand A of formula I (2.5 mmol, i.e. 5 equivalents with respect to P)
  anhydrous 3PN: 1.21 g (15 mmol, i.e. 30 equivalents)
  $Ni(cod)_2$: 138 mg (0.5 mmol, 1 equivalent)
  Lewis acid, amount and nature indicated in Table 1 below.

The ligands A used in the examples are:
Tris(2-thienyl)phosphine: sold by the company Aldrich

EXAMPLE 8

Hydrocyanation of 3-PN to Give AdN

The following are successively charged, under an argon atmosphere, to a 60 ml glass tube of Shott type, equipped with a septum stopper:
  tris(2-thienyl)phosphine (1.25 mmol, i.e. 2.5 equivalents with respect to P)
  tris(2-furyl)phosphine (1.25 mmol, i.e. 2.5 equivalents with respect to P)
  anhydrous 3PN: 1.21 g (15 mmol, i.e. 30 equivalents)
  $Ni(cod)_2$: 138 mg (0.5 mmol, 1 equivalent)
  diphenylboronic anhydride 91 mg (0.25 mmol, i.e. 0.5 equivalent) as Lewis acid.

The mixture is brought to 70° C. with stirring. Acetone cyanohydrin is fed into the reaction medium via a syringe driver at a flow rate of 0.45 ml per hour. After 3 hours, the injection is stopped. The mixture is cooled to ambient temperature, diluted with acetone, and analysed by gas chromatography.

The linearity measured is 87.6% for a dinitrile yield RY(DN) of 22.2%.

The invention claimed is:

1. A process for the hydrocyanation of a hydrocarbon-based compound having at least one site of ethylenic unsaturation comprises reaction thereof, in a liquid medium, with hydrogen cyanide in the presence of a catalyst comprising a metal element selected from among the transition metals and at least one organophosphorus ligand, wherein said at least one organophosphorus ligand comprises at least one compound having the general formula (I):

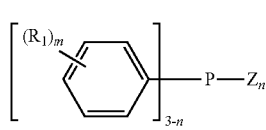

in which:
Z is an aromatic or non-aromatic, substituted or unsubstituted, 5- or 6-atom cyclic moiety containing a nitrogen or sulfur atom and the bond with the phosphorus atom is borne by the carbon in the alpha-position with respect to the heteroatom,
n is an integer ranging from 1 to 3,
m is an integer ranging from 0 to 5, and
R1 is a hydrogen atom, a linear or branched alkyl radical, that may contain heteroatoms, having from 1 to 12 carbon atoms, a substituted or unsubstituted aromatic or cycloaliphatic radical that may comprise heteroatoms, a carbonyl, alkoxycarbonyl or alkoxy radical, a halogen atom, a nitrile group or a haloalkyl radical having from one to 12 carbon atoms.

2. The process as defined by claim 1, wherein in formula (I), Z is a thienyl, pyrrolyl or pyridyl radical.

3. The process as defined by claim 1, wherein the at least one compound of general formula (I) comprises one of the formulae below:

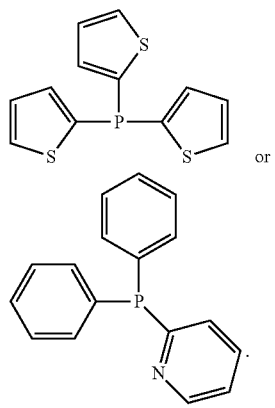

4. The process as defined by claim 1, wherein the metal element is selected from the group consisting of nickel, cobalt, iron, ruthenium, rhodium, palladium, osmium, iridium, platinum, copper, silver, gold, zinc, cadmium and mercury.

5. The process as defined by claim 1, wherein said catalytic system has the general formula (II):

$$M[L_f]_t \qquad (II)$$

in which:
M is a transition metal,
$L_f$ comprises the organophosphorus ligand(s), at least one of which is a compound of formula (I), and
t is a number ranging from 1 to 10 (limits included).

6. The process as defined by claim 1, wherein the organic compound having at least one ethylenic double bond is selected from among diolefins, butadiene, isoprene, 1,5-hexadiene, 1,5-cyclooctadiene, ethylenically unsaturated aliphatic nitriles, linear pentenenitriles, 3-pentenenitrile, 4-pentenenitrile, monoolefins, styrene, methylstyrene, vinylnaphthalene, cyclohexene, methylcyclohexene, and mixtures thereof.

7. The process as defined by claim 1, wherein the amount of nickel compound or of compound of another transition metal is selected such that from $10^{-4}$ to 1 mol of nickel or of the other transition metal are used per mole of organic compound to be hydrocyanated or isomerized, and the amount of organophosphorus compound present is selected such that the number of moles of this compound relative to 1 mol of transition metal ranges from 0.5 to 100.

8. The process as defined by claim 1, comprising hydrocyanation into dinitriles, by reacting an ethylenically unsaturated nitrile compound with hydrogen cyanide, carried out in the presence of a catalytic system comprising at least one compound of a transition metal, at least one phosphine of formula (I), and a co-catalyst comprising at least one Lewis acid.

9. The process as defined by claim 8, wherein the ethylenically unsaturated nitrile compound is selected from among ethylenically unsaturated aliphatic nitriles comprising linear pentenenitriles, 3-pentenenitrile, 4-pentenenitrile, and mixtures thereof.

10. The process as defined by claim 8, wherein the Lewis acid co-catalyst is selected from among the compounds of elements from Groups Ib, IIb, IIIa, IIIb, IVa, IVb, Va, Vb, VIb, VIIb and VIII of the Periodic Table of Elements.

11. The process as defined by claim 8, wherein the Lewis acid is selected from among zinc chloride, zinc bromide, zinc iodide, manganese chloride, manganese bromide, cadmium chloride, cadmium bromide, stannous chloride, stannous bromide, stannous sulfate, stannous tartrate, indium trifluoromethylsulphonate, chlorides or bromides of rare earth elements selected from among lanthanum, cerium, praseodymium, neodymium, samarium, europium, gadolinium, terbium, dysprosium, hafnium, erbium, thallium, ytterbium, lutetium, cobalt chloride, ferrous chloride, yttrium chloride, organometallic compounds, and mixtures thereof.

12. The process as defined by claim 1, comprising isomerization into pentenenitriles, of the 2-methyl-3-butenenitrile present in the reaction mixture emanating from the hydrocyanation of butadiene carried out in the absence of hydrogen cyanide, but in the presence of a catalyst comprising at least one compound of formula (I) and at least one compound of a transition metal.

* * * * *